United States Patent [19]

Marcus et al.

[11] Patent Number: 5,037,386
[45] Date of Patent: Aug. 6, 1991

[54] PRESSURE SENSING SCOPE CANNULA

[75] Inventors: Herbert D. Marcus, Winchester; Allen H. DeSatnick; Paul A. Torrie, both of Marblehead, all of Mass.

[73] Assignee: Minnesota Mining and Manufacturing Company, St. Paul, Minn.

[21] Appl. No.: 437,839

[22] Filed: Nov. 17, 1989

[51] Int. Cl.[5] .................................................. A61M 3/00
[52] U.S. Cl. ...................................... 604/43; 604/280; 604/118; 128/4
[58] Field of Search ................. 604/19, 21, 22, 27, 604/28, 30, 35, 43, 118, 264, 280, 282, 326; 128/4 A, 657

[56] References Cited

U.S. PATENT DOCUMENTS

| | | |
|---|---|---|
| 2,038,393 | 4/1936 | Wappler . |
| 3,081,770 | 3/1963 | Hunter . |
| 3,610,226 | 10/1971 | Albisser . |
| 3,835,842 | 9/1974 | Iglesias . |
| 3,850,162 | 11/1974 | Iglesias . |
| 3,850,175 | 11/1974 | Iglesias . |
| 3,900,022 | 8/1975 | Widran . |
| 4,132,227 | 1/1979 | Ibe ............................................ 128/4 |
| 4,160,448 | 7/1979 | Jackson . |
| 4,180,068 | 12/1979 | Jacobsen et al. . |
| 4,368,348 | 1/1983 | Eichelberger et al. . |
| 4,423,727 | 1/1984 | Widran et al. . |
| 4,524,808 | 6/1985 | Fleischer et al. . |
| 4,603,699 | 8/1986 | Himpens . |
| 4,637,389 | 1/1987 | Heyden ........................ 128/207.15 |
| 4,650,462 | 3/1987 | DeSatnick et al. . |
| 4,686,984 | 8/1987 | Bonnet . |
| 4,710,181 | 12/1987 | Fuqua ................................ 604/280 |
| 4,750,902 | 6/1988 | Wuchinich et al. ................ 604/22 |
| 4,769,018 | 9/1988 | Wilson . |
| 4,795,439 | 1/1989 | Guest ................................. 604/43 |
| 4,820,265 | 4/1989 | DeSatnick et al. . |
| 4,850,373 | 7/1989 | Zatlovkal et al. .................. 128/749 |
| 4,904,246 | 2/1990 | Atkinson ........................... 604/264 |
| 4,954,129 | 9/1990 | Giuliani et al. ..................... 604/53 |
| 4,955,375 | 9/1990 | Martinez ........................ 128/207.15 |
| 4,973,321 | 11/1990 | Michelson ........................ 604/280 |

Primary Examiner—John D. Yasko
Assistant Examiner—Adam J. Cermak
Attorney, Agent, or Firm—Gary L. Griswold; Walter N. Kirn; Robert W. Hoke, II

[57] ABSTRACT

An arthroscope cannula including inner and outer intimately engaged concentric tubes with the inner tube having a longitudinally extending wall depression defining, in conjunction with the outer tube, a pressure passage. The inner tube receives the scope which is restrained therein by the wall depression to define an inflow fluid passage. The outer tube is selectively removable from about the inner tube with both tubes mounting on and projecting from a flow controlling and directing bridge assembly.

12 Claims, 2 Drawing Sheets

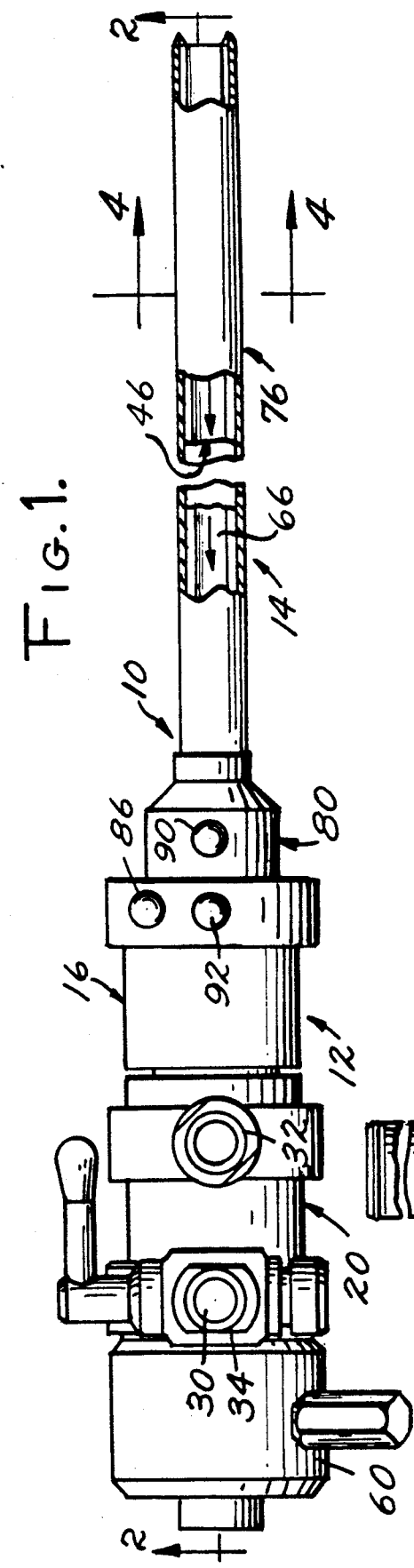
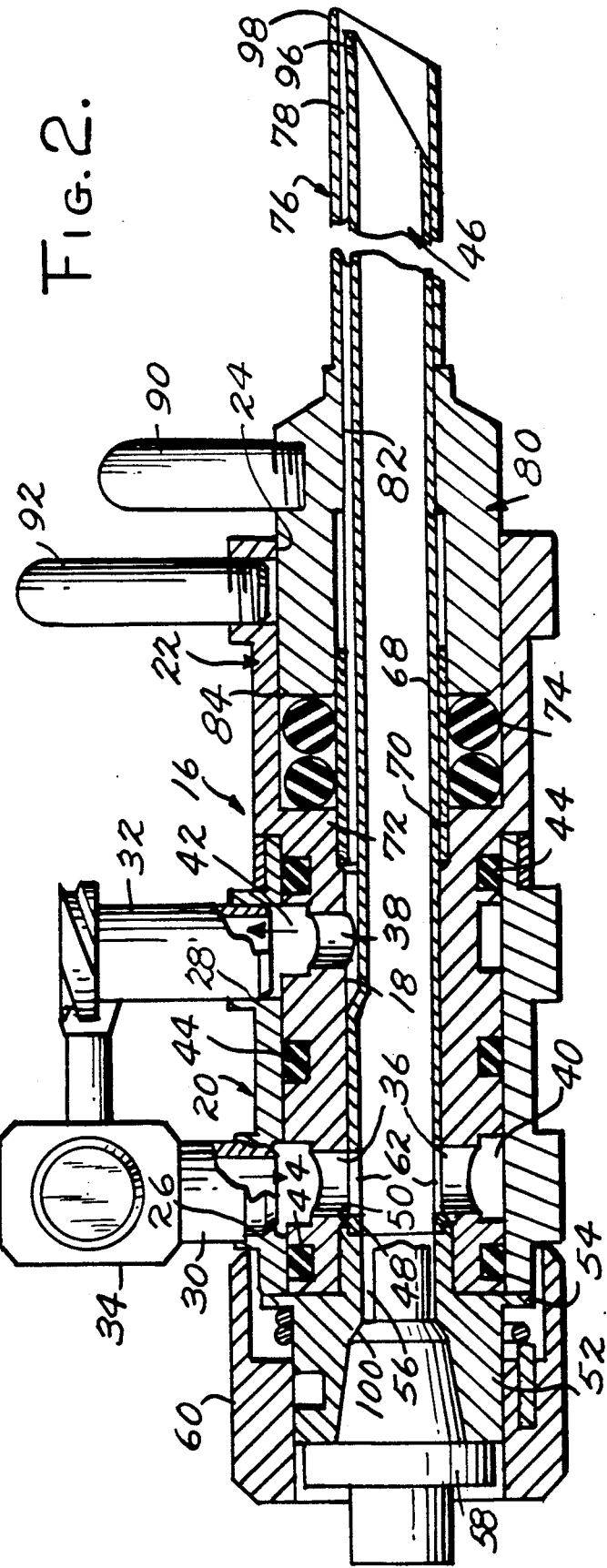

PRESSURE SENSING SCOPE CANNULA

BACKGROUND OF THE INVENTION

The present invention is broadly concerned with cannula devices, and more particularly relates to cannula assemblies for use in arthroscopy or similar medical or surgical procedures wherein the sensing of pressure in the body joint or at the site of the procedure is a factor.

U.S. Pat. Nos. 4,650,462 and 4,820,265, are directed to equipment for use in arthroscopic procedures, which procedures are generally described in the patents. Such procedures have resulted in the development of number of special purpose cannulas for inflow and outflow of fluid, as well as for pressure sensing in the joint, including:

1. A dedicated pressure sensing cannula which is inserted into the joint in the manner of a large hypodermic needle, and connected to a pressure sensing line, as for example, noted in the tube set of U.S. Pat. No. 4,820,265.
2. A dedicated outflow cannula comprising a tube between 3 mm and 6 mm in diameter which is inserted in the joint and connected to the outflow line.
3. A combination inflow cannula consisting of concentric tubes with the inner tube approximately 3 mm and the outer tube approximately 4 mm in diameter. A small annulus is defined between the tubes which is used to sense the fluid pressure in the joint. The larger inside diameter of the inner tube carries the inflow from the input tube of the pump.
4. A combination outflow cannula which is similar to the combination inflow cannula except that the inner tube carries the outflow from the joint while the annulus senses the pressure.

In an arthroscopic procedure, there is always at least one additional cannula involved, the arthroscope cannula in which the scope or viewing instrument is positioned. This cannula will normally incorporate means for fluid communication with the joint provided by the space defined between the outside diameter of the inserted arthroscope and the inside diameter of the arthroscope cannula tube.

From the above, it will be recognized that the doctor has many choices for setting up the joint for the arthroscopic procedure. Some of the most common are:

1. Inflow through the arthroscope cannula, pressure sensing by a dedicated pressure sensing cannula, and outflow by a dedicated outflow cannula.
2. Inflow and pressure sensing through a combination inflow cannula, and outflow through the arthroscope cannula.
3. Inflow through the arthroscope cannula, and outflow and pressure sensing through a combination outflow cannula.

Methods 2 and 3 above are the ones most favored by doctors since only two incisions are required, as opposed to three incisions for method 1. A desirable alternative to methods 2 and 3, recognized in the development of the present invention, would be the incorporation of pressure sensing in an arthroscope cannula. Only two portals or incisions would be required, with inflow and pressure sensing in the arthroscope cannula, and outflow using a dedicated outflow cannula. This has a big safety advantage since both pressure sensing and inflow occur together. The same safety advantage is present in method 2 above, however, suction may be required to assist outflow.

An initial proposal was to use concentric tubes with an annular passage provided therebetween in the manner of the combination inflow and outflow cannulas. As far as the fluid control system was concerned, the cannula was acceptable. However, because of its manner of construction, with the spaced concentric tubes, a little over 1 millimeter was added to the diameter of the arthroscope cannula. This was considered undesirable and unacceptable to the doctors/users of the device. Thus the problem still remained as to how to provide for acceptable pressure sensing utilizing the arthroscope cannula.

SUMMARY OF THE INVENTION

The arthroscope cannula of the present invention provides a pressure sensing channel therein without increasing the overall diameter of the cannula tube assembly. In other words, notwithstanding the incorporation of a pressure sensing channel in an arthroscope cannula, a desired overall tube diameter of approximately 5 mm can be maintained. The resultant cannula is within acceptable diameter parameters, allows use of only two incisions in the actual medical procedure, and incorporates the significant safety advantage of pressure sensing and inflow occurring together.

Basically, the pressure sensing scope cannula of the invention, while using concentric inner and outer tubes, provides that each of these tubes have a wall thickness of approximately ¼ mm or 0.010 to 0.012 inches, which is in turn approximately one half of the wall thickness of a conventional arthroscope cannula. The concentric tubes are sized to engage, one within the other, without space therebetween, and with a tolerance sufficient only to allow for telescoping engagement of the outer tube over the inner tube.

In order to provide the fluid path for pressure sensing, the wall of the inner tube, for substantially the full effective length thereof rearward from the forward or leading end, is inwardly dimpled or depressed to a depth of approximately 0.025 inches or 0.635 mm along a narrow arc approximately 0.090 inches or 2.29 mm wide. This defines a fluid pressure receiving channel comprising a linear flow passage between and along the otherwise intimately engaged inner and outer tubes. The depth of the dimpling is equal to the height of the arc thereover and is formed without distortion of the circular configuration of the inner tube. The pressure channel is formed without an increase in the overall external diameter of the cannula tube assembly. The arthroscope is in turn generally restrained or retained in position in the inner tube by the longitudinal inwardly directed dimple or depression whereby considerable fluid inflow area is provided about the scope.

In addition to incorporating the pressure sensing channel with no increase in overall diameter, there is also no decrease in the structural strength of the cannula and no significant variance in the size of the inflow passage.

Additional advantages residing in the utilization of two separate tubes in the formation of the scope cannula include convenient disassembly for cleaning, particularly in the restrictive area of the pressure sensing passage. If the pressure sensing passage were formed by an internal rib or partition, adequate cleaning thereof would be substantially impossible. A further advantage of the separability of the tubes is the manner of insertion of the cannula. In other words, the outer tube can be inserted into the joint capsule using a round obturator therein for smooth and easy insertion. The obturator can then be removed and the inner tube inserted.

Additional objects and advantages of the invention will become apparent from the following detailed discussion of the construction and manner of use of the pressure sensing scope cannula with specific reference to the accompanying drawings.

BRIEF DESCRIPTION OF THE DRAWINGS

FIG. 1 is an elevation view of the arthroscope cannula with portions broken away for purposes of illustration;

FIG. 2 is an enlarged cross-sectional view, with portions in elevation, of the cannula taken substantially on a plane passing along line 2—2 in FIG. 1;

DESCRIPTION OF PREFERRED EMBODIMENT

Figure 3:
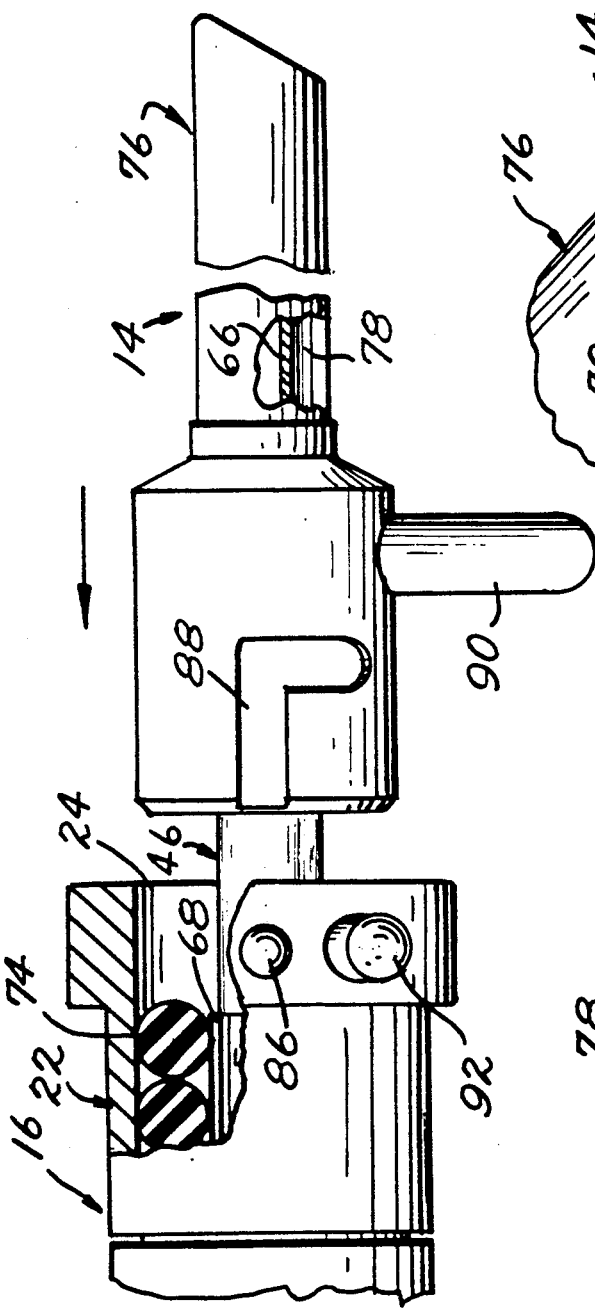
FIG. 3 is an elevation view, partially in section, illustrating the outer tube disengaged and forwardly shifted.
Figure 5:
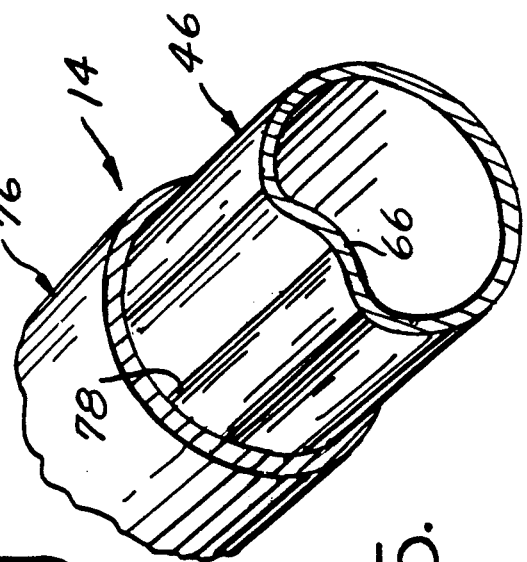
FIG. 5 is a perspective detail of the telescope inner and outer tubes with the defined pressure passage.

The pressure sensing scope cannula 10 includes a bridge assembly 12 and a tube assembly 14 in fluid communication with the bridge assembly and forwardly extending therefrom for selective reception within the body of a patient.

The bridge assembly 12 includes an elongate cylindrical fixed bridge 16 with a central bore 18 longitudinally therethrough. An elongate sleeve-like rotating bridge 20 is closely received about the fixed bridge 16 along a major portion of the length thereof, forward from the rear or proximal end. Immediately forward of the rotating bridge 20, the fixed bridge includes a radially enlarge leading end portion 22 defining a forwardly opening cylindrical chamber 24 of a substantially greater internal diameter than the internal diameter of the bore 18. This leading end portion mounts the tube assembly 14 and also defines an abutment to longitudinally position the rotating bridge 20 on the fixed bridge 16.

The rotating bridge 20 includes a pair of rear and forward longitudinally spaced openings 26 and 28 therein, and a pair of fluid lines 30 and 32 engaged within the openings 26 and 28, for example by threading therein in a fluid-tight manner. The line 30, provided with a flow-controlling valve 34 with an operating handle, is adapted to couple to an appropriate source of fluid and constitute an inflow line. The line 32 is adapted to communicate with appropriate pressure sensing means and constitutes a pressure sensing line.

Each of the openings 26 and 28 in the rotating bridge 20, in at least one rotated position thereof, aligns with a port or opening 36, 38 radially through the fixed bridge 16 and into communication with the bore 18 therethrough. An annular recess 40, 42 is defined in the fixed bridge in alignment with each of the ports 36, 38 whereby fluid communication is maintained between each of the lines 30 and 32 and the interior of the bore 18 regardless of the rotational position of the rotating bridge 20. In this manner, adjustments as desired may be made in the alignment of the fluid lines 30 and 32. Appropriate annular elastomer seals 44 are provided to the opposite sides of the ports 36, 38 and associated recesses 40, 42 to preclude fluid leakage and provide for frictionally restrictive rotation of the rotating bridge 20 about the fixed bridge 16. The seals 44 also provide for a retention of the rotating bridge in any rotated adjusted position until manually moved therefrom.

The forwardly extending tube assembly 14 includes an elongate hollow cylindrical inner tube 46 having a flared proximal or rear end 48. The inner tube 46 is longitudinally received through the fixed bridge bore 18 inwardly through the proximal end thereof with the proximal end 48 of the tube 46 seating and sealing against an appropriate annular seat 50 defined within the proximal end of the bore 18 immediately rearward of the rearmost port or ports 36. The inner tube 46 will in turn be retained within the fixed bridge by an end plug 52 mounted immediately rearward thereof and in engagement with the proximal end of the tube 46. As desired, the end plug can be mounted by threaded engagement within the bore 18 rearward of the enlarged end 48 of the tube 46, the bore, at the rear end thereof, being appropriately enlarged to accommodate the enlarged tube end 48 and the threaded shank portion of the end plug 52. The end plug 52 will also incorporate an annular flange 54 which, upon a mounting of the end plug 52, engages against the proximal or rear end of the rotating bridge 20 for a longitudinal retention of the bridge. The end plug 52 includes a central bore 56 therethrough aligned with the bore 18 for reception of an arthroscope or like medical instrument 58 as shall be referred to in greater detail subsequently. The rear portion of the plug bore 56 will be appropriately tapered or configured to conform to the mounting end of the scope 58 which in turn will be releasably retained by an appropriate rotatable lock assembly 60 of conventional construction.

The inner tube 46, at the proximal end portion thereof immediately forward of the mounting end 48, includes at least one lateral opening 62 therein alignable with a rotating bridge rear port 36. Opposed or multiple openings 62 can be provided for alignment with an equal number of ports 36. As will be appreciated, the communication will be maintained throughout all rotated positions of the rotating bridge 20 relative to the fixed bridge 16 through the annual recess 40.

The inner tube 46, forward of the openings 62, and between the inflow line ports 36 and the pressure line ports 38 forward thereof, is cylindrically sealed to the bore 18.

The inner tube 46, from the pressure line port 38 to the forward or distal end of the tube 46 is provided with a linearly extending dimple or depression 66 approximately 0.025 inches or 0.635 mm deep and 0.090 inches or 2.29 mm wide, which defines a pressure sensing channel in the otherwise completely cylindrical tube wall. This channel opens forwardly of the distal end of inner tube 46 and, within the fixed bridge 16, communicates directly and solely with the pressure line port 38.

Mounted within the forwardly opening chamber 24 of the enlarged forward portion 22 of the fixed bridge 16 is a seal tube 68 of cylindrical configuration which closely conforms to the cylindrical exterior configuration of the inner tube 46, spanning the depression 66 therein. The seal tube 68 has the rear portion thereof received and adhesively secured within an annular seat 70 within an inner wall 72 of the fixed bridge 16 immediately forward of the pressure line port 38. The seal tube 68 extends to approximately midpoint within the chamber 24 and is surrounded by an elastomer seal or seals 74 which engage against the forward face of the bridge wall 72.

The tube assembly 14 also includes an outer cylindrical tube 76 approximately 5 mm or 0.20 inches in diameter concentrically receivable in sliding fluid-tight relationship on the inner tube 46. The channel formed by the linear inwardly depressed portion 66 of the wall of the inner tube 46 defines, with the overlying wall of the outer tube 76, a closed elongate fluid passage 78 for pressure sensing which constitutes a minimal portion of the cross-sectional area of the tube assembly. As will be appreciated, this passage 78 opens through the forward leading end of the cannula 10, or more particularly the tube assembly 14. At its proximal or rear end, the pressure sensing passage 78 communicates directly with the pressure line 32 through the pressure line port 38.

The outer tube 76 is releasably mounted by means of a cylindrical mounting head 80 on and fixedly sealed to the proximal end portion of the tube 76. This mounting head, including a hollow bore 82 therethrough in alignment with the hollow outer tube 76, is telescopically received within the forwardly opening chamber 24 of the leading end portion 22 of the fixed bridge 16 and into sealing engagement with the elastomer seals 74 about the tube seal 68. The proximal or near end of the mounting head 80 may be peripherally beveled, as at 84, to facilitate alignment with and introduction into the chamber 24 and for enhanced sealing engagement with the seals 74, which, in an obvious manner, expand under pressure to effect the desired fluid tight seal. Appropriate lock means, in the nature of a bayonet lock including a radially inwardly projecting lug 86 on the chamber wall and corresponding right angle slot 88 in the exterior surface of the mounting head 80, releasably lock the mounting head 80 in its mounted position. Manipulation of the head 80 relative to the fixed bridge 16 is facilitated by a laterally extending pin-like handle 90 on the mounting head sufficiently forward to not interfere with the full extension of the mounting head 80 into the receiving chamber 24. A similar manipulating pin handle 92 may be provided on the leading end portion 22 of the fixed bridge 16. When mounted and sealed, through the elastomer seal 74, the pressure passage 78, extending through seal tube 68, is in fluid communication solely with the pressure line port 38.

Figure 4:
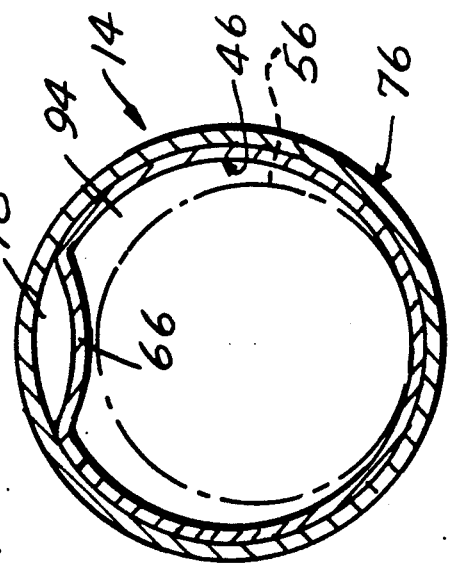
FIG. 4 is an enlarged cross-sectional view taken substantially on a plane passing along line 4—4 in FIG. 1 through the concentric cannula tubes and with a scope schematically positioned therein.

Referring specifically to the cross-sectional detail of FIG. 4, the tube assembly 14 is of a size, and utilized in the manner of known arthroscope cannulas insofar as longitudinally receiving a scope 58 therethrough and defining an inflow passage 94 between the scope and immediate inner tube diameter. In addition thereto, the tube assembly of the invention uniquely provides for the segregated pressure passage 78 by the expedient of using intimately engaged concentrically telescopic tubes with the inner tube 46 longitudinally recessed along a restricted linear extent thereof. By defining the pressure passage in this manner, and utilizing wall thicknesses for the inner and outer tubes which are each approximately one half the thickness of the tube wall of a standard arthroscope cannula, the outside diameter of the tube assembly is maintained equivalent to that of the conventional arthroscope cannula. Further, through the intimate engagement of the tubes without space therebetween other than in the pressure passage, the structural integrity of the tube assembly is significant and at least equal to that of a single tube arthroscope cannula.

Noting FIG. 2, the leading ends of the inner and outer tubes 46 and 76 are tapered rearwardly from forwardmost tip portions of 96 and 98 respectively. These tip portions 96 and 98, in the assembled cannula, are radially adjacent each other with the pressure passage 78 defined therebetween and opening through the forwardmost extent of the leading end of the cannula. In other words, the linear depression in the inner tube 46 is aligned with and opens forwardly through the forwardmost tip portion 96 of inner tube 46. The inner tube tip portion 96 in turn aligns with the forwardmost tip portion 98 of the outer tube. Such an arrangement provides a significant safety feature in that, even if the scope is partially withdrawn from the joint capsule, the pressure sensing passage will still be positioned to sense the pressure in the joint capsule. If the pressure sensing passage was positioned 180 degrees from the forwardmost tip portions, the sensing passage would be the first thing withdrawn from the joint capsule and would no longer be sensing pressure in the joint capsule even though the cannula is still at least partially operatively engaged therein.

The separability of the tubes is important in allowing for proper cleaning and sterilization of the instrument. For example, if the outer tube were not removable, it would be impossible to adequately clean the pressure sensing passage. Further, because of the separability of the tubes, the outer tube can be inserted into a body joint using a round obturator positioned for smooth and easy insertion. The obturator can then be removed and the inner tube inserted to complete the assembly of the cannula.

The defined linear depression 66 within the inner tube 46 also restrains and generally positions and stabilizes the scope within the inner tube in a manner whereby a stable inflow passage 94 is maintained thereabout. Noting FIG. 4, it will be seen that most of the area available for fluid flow in the inflow passage 94 is adjacent the depression 66 and thus adjacent the pressure sensing passage 78. The passage 94 narrows considerably as it extends circumferential away from the depression 66 to the diametrically opposed portion of the inner tube 46. This narrowing of the inflow passage is a direct result of the positioning and retention of the scope in substantially tangential contact with the inner surface of the inner tube 46 by the depression 66. Thus, very little flow occurs in this area remote from the pressure sensing passage 78. Such an arrangement and passage relationship is considered to provide the optimum configuration for safety and efficacy in that the pressure is being measured as close as possible to the point of maximum flow introduction. Additionally, the relationship between the passages is such whereby the pressure in the joint capsule is sensed concurrently and continuously with flow introduction into the joint capsule until such time as the leading end of the cannula is completely removed from the joint capsule.

The actual introduction of the scope 58 into the cannula is effected in a substantially conventional manner through the rear of the bridge assembly with the scope releasably locked into operative position by the lock assembly 60. Note the schematic showing of the proximal end of a mounted scope 58 in FIG. 2. In mounting the scope, the rear portion of the bridge assembly bore 18 is sealed as at 100 to preclude rearward discharge of the inflow fluid and restrict the flow to move forwardly from the inflow line 30 through the inner tube.

From the foregoing, it will be appreciated that construction of the cannula in the manner described provides for a unique dual tube cannula within a given acceptable outer diameter, with no loss of strength and with only minimal and insignificant loss of tube area, along with the advantages of a practical pressure sensing arthroscope cannula enabling utilization of a single incision for inflow, pressure sensing, and the scope itself.

We claim:

1. For use in receiving and positioning a medical instrument during a surgical procedure, a pressure sensing scope cannula comprising a bridge assembly, a pair of elongate concentric inner and outer hollow tubes defining a longitudinal axis along their lengths, said inner tube including a proximal end portion fixed to said bridge assembly and a forward end adapted for reception within the body of a patient, said inner tube defining a hollow interior for receiving and guiding a medical instrument introduced therethrough, a linear depression in said inner tube comprising a minor portion of the circumference of said inner tube and extending longitudinally therealong proximally from the forward end of the inner tube, said inner tube forming a fluid passage, a fluid port in said bridge assembly communicating with the fluid passage of said inner tube at the proximal end portion of the inner tube, said outer tube being slidably received over said inner tube and, other than for the linear depression in said inner tube, being in fluid-tight relation therewith, said outer tube overlying said depression and defining therewith a peripherally closed pressure passage independent of said inner tube fluid passage, said bridge assembly including a pressure port communicating with the pressure passage, said linear depression forming a lateral restraint within said inner tube for laterally positioning and retaining a received medical instrument in said inner tube diametrically opposed from said depression with said fluid passage within said inner tube being defined about the received medical instrument and principally adjacent said depression and said pressure passage.

2. The cannula of claim 1 wherein said outer tube includes a proximal end and a forward end, means at the proximal end of said outer tube for mounting and sealing said outer tube to said bridge assembly, the forward end of the mounted outer tube being generally coextensive with the forward end of the inner tube.

3. The cannula of claim 2 wherein the forward ends of said inner and outer tubes are rearwardly tapered and define a forwardmost tip portion on each of said forward ends of said inner and outer tubes, said tip portions being radially aligned and adjacent each other with the pressure passage defined therebetween, extending to and opening forwardly of said forwardmost tip portions.

4. A pressure sensing scope cannula comprising a bridge assembly, a pair of elongate concentric inner and outer hollow tubes defining a longitudinal axis along their lengths, said inner tube including a proximal end portion fixed to said bridge assembly and a forward end adapted for reception within the body of a patient, said inner tube defining a hollow interior for receiving and guiding a medical instrument introduced therethrough, a linear depression in said inner tube comprising a minor portion of the circumference of said inner tube and extending longitudinally therealong proximally from the forward end of the inner tube, said inner tube forming a fluid passage, a fluid port in said bridge assembly communicating with the fluid passage of said inner tube at the proximal end portion of the inner tube, said outer tube being slidably received over said inner tube and, other than for the linear depression in said inner tube, being in fluid-tight relation therewith, said outer tube overlying said depression and defining therewith a peripherally closed pressure passage independent of said inner tube fluid passage, said bridge assembly including a pressure port communicating with the pressure passage, said linear depression forming a lateral restraint within said inner tube for laterally retaining a received medical instrument in said inner tube diametrically opposed from said depression with said fluid passage within said inner tube being defined about the received medical instrument and principally adjacent said depression and said pressure passage, said outer tube including a proximal end and a forward end, means at the proximal end of said outer tube for mounting and sealing said outer tube to said bridge assembly, the forward end of the mounted outer tube being generally coextensive with the forward end of the inner tube, said bridge assembly including a proximal end and a distal end with a longitudinal bore through said bridge assembly therebetween, said fluid port and said pressure port communicating laterally with said bore, said fluid port being closer to the proximal end of the bridge assembly than said pressure port, said inner tube being received within said bore with the proximal end portion of the inner tube adjacent the fluid port in the bridge assembly, said inner tube, between said fluid port and said pressure port, being sealed to said bore completely about the periphery of the inner tube to preclude fluid passage between the ports.

5. The cannula of claim 4 wherein said linear passage terminates at a proximal end at and in communication with said pressure port.

6. The cannula of claim 5 wherein the means at the proximal end of the outer tube for mounting and sealing the outer tube to the bridge assembly comprises a forwardly opening chamber in said bridge assembly generally coaxial with and in direct communication with said longitudinal bore, and a mounting head on the proximal end of said outer tube telescopically receivable within said chamber, said mounting head including a bore therethrough directly communicating the outer tube with the bridge bore upon a reception of the mounting head in said chamber, and lock means releasably locking said mounting head within said chamber.

7. In an arthroscopic cannula, a tube assembly including concentric inner and outer tubes defining a longitudinal axis along their lengths, said inner tube being adapted to receive a scope therethrough and define a longitudinal inflow fluid passage outward of the scope and within said inner tube, and a pressure sensing passage defined longitudinally between said inner and outer tubes independent of said inflow fluid passage, said pressure sensing passage being defined by a longitudinal depression in said inner tube, said depression extending linearly along said inner tube and being of an arcuate width comprising a minor portion of the circumference of said inner tube, said inner and outer tubes, other than for said depression, being in peripheral fluid-tight engagement, said inner and outer tubes having tapered forward ends defining a forwardmost tip portion on each tube, said tip portions being radially aligned and adjacent each other, said pressure sensing passage being aligned between, extending to and opening forwardly through said forwardmost tip portions.

8. The cannula of claim 7 wherein said depression extends into the fluid passage within said inner tube and comprises a means for laterally retaining a scope within the inner tube diametrically opposed to said depression with the major area of the fluid passage being defined adjacent to said depression and adjacent said pressure sensing passage.

9. The cannula of claim 7 including means for communicating the fluid passage with a source of inflow fluid, and means for communicating the pressure sensing passage with pressure sensing means.

10. In an arthroscopic cannula, a tube assembly including concentric inner and outer tubes defining a longitudinal axis along their lengths, said inner tube being adapted to receive a scope therethrough and define a longitudinal inflow fluid passage outward of the scope and within said inner tube, and a pressure sensing passage defined longitudinally between said inner and outer tubes independent of said inflow fluid passage, said pressure sensing passage being defined by a longitudinal depression in said inner tube, said depression extending linearly along said inner tube and being of an arcuate width comprising a minor portion of the circumference of said inner tube, said inner and outer tubes, other than for said depression, being in peripheral fluid-tight engagement, said depression extending into the fluid passage within said inner tube and comprising a means for laterally retaining a scope within the inner tube diametrically opposed to said depression with the major area of the fluid passage being adjacent to said depression and adjacent said pressure sensing passage, said inner and outer tubes having tapered forward ends defining a forwardmost tip portion on each tube, said tip portions being radially aligned and adjacent each other, said pressure sensing passage being aligned between and opening forwardly through said tip portions.

11. A pressure sensing scope cannula comprising a bridge assembly, a pair of elongate concentric inner and outer hollow tubes defining a longitudinal axis along their lengths, said inner tube including a proximal end portion fixed to said bridge assembly and a forward end adapted for reception within the body of a patient, said inner tube defining a hollow interior for receiving and guiding a medical instrument introduced therethrough, a linear depression in said inner tube comprising a minor portion of the circumference of said inner tube and extending longitudinally therealong proximally from the forward end of the inner tube, said inner tube forming a fluid passage, a fluid port in said bridge assembly communicating with the fluid passage of said inner tube at the proximal end portion of the inner tube, said outer tube being slidably received over said inner tube and, other than for the linear depression in said inner tube, being in fluid-tight relation therewith, said outer tube overlying said depression and defining therewith a peripherally closed pressure passage independent of said inner tube fluid passage, said bridge assembly including a pressure port communicating with the pressure passage, said bridge assembly further including a proximal end and a distal end with a longitudinal bore through said bridge assembly therebetween, said fluid port and said pressure port communicating laterally with said bore, said fluid port being closer to the proximal end of the bridge assembly than said pressure port, said inner tube being received within said bore with the proximal end portion of the inner tube adjacent the fluid port in the bridge assembly, said inner tube, between said fluid port and said pressure port, being sealed to said bore completely about the periphery of the inner tube to preclude fluid passage between the ports.

12. For use in receiving and positioning a medical instrument during a surgical procedure, an arthroscopic cannula comprising a tube assembly including a concentric inner and outer tubes with open, substantially coextensive distal ends and defining a longitudinal axis along their lengths, said inner tube forming a longitudinal inflow fluid passage and being adapted to receive a medical instrument therethrough with the longitudinal inflow fluid passage being defined outward of the medical instrument and within said inner tube and a pressure sensing passage defined longitudinally between said inner and outer tubes independent of said inflow fluid passage, said pressure sensing passage being defined by a self-sustaining longitudinal depression in said inner tube, said depression extending linearly along said inner tube and being of an arcuate width comprising a minor portion of the circumference of said inner tube, said depression having an open distal end at the distal ends of said inner and outer tubes, said inner and outer tubes, other than for said depression, being in peripheral fluid-tight engagement, said depression extending into the fluid passage within said inner tube and comprising a means for laterally positioning and retaining the medical instrument within the inner tube diametrically opposed to said depression with the major area of the fluid passage being defined adjacent to said depression and adjacent said pressure sensing passage.

* * * * *